(12) United States Patent
Nazzaro et al.

(10) Patent No.: US 7,491,231 B2
(45) Date of Patent: Feb. 17, 2009

(54) ONE-BRANCH STENT-GRAFT FOR BIFURCATED LUMENS

(75) Inventors: Patrice Nazzaro, Hoboken, NJ (US); Dennis Kujawski, Warwick, NY (US)

(73) Assignee: SciMed Life Systems, Inc., Maple Grove, MN (US)

( * ) Notice: Subject to any disclaimer, the term of this patent is extended or adjusted under 35 U.S.C. 154(b) by 490 days.

(21) Appl. No.: 10/963,354

(22) Filed: Oct. 12, 2004

(65) Prior Publication Data

US 2005/0049676 A1 Mar. 3, 2005

Related U.S. Application Data

(62) Division of application No. 10/461,898, filed on Jun. 13, 2003, now abandoned.

(51) Int. Cl.
*A61F 2/06* (2006.01)
(52) U.S. Cl. ............... 623/1.35; 623/1.13
(58) Field of Classification Search ....... 623/1.35–1.37, 623/1.13
See application file for complete search history.

(56) References Cited

U.S. PATENT DOCUMENTS

| | | | |
|---|---|---|---|
| 3,657,744 A | 4/1972 | Ersek | |
| 4,530,113 A | 7/1985 | Matterson | |
| 4,731,073 A | 3/1988 | Robinson | |
| 5,360,443 A | 11/1994 | Barone et al. | |
| 5,397,345 A | 3/1995 | Lazarus | |
| 5,405,379 A | 4/1995 | Lane | |
| 5,464,449 A | 11/1995 | Ryan et al. | |
| 5,476,506 A | 12/1995 | Lunn | |
| 5,522,880 A | 6/1996 | Barone et al. | |
| 5,609,627 A | 3/1997 | Goicoechea et al. | |
| 5,628,783 A | 5/1997 | Quiachon et al. | |
| 5,639,278 A * | 6/1997 | Dereume et al. ........... 623/1.13 |
| 5,656,036 A | 8/1997 | Palmaz | |
| 5,665,117 A | 9/1997 | Rhodes | |
| 5,676,697 A | 10/1997 | McDonald | |
| 5,683,449 A | 11/1997 | Marcade | |
| 5,683,450 A | 11/1997 | Goicoechea et al. | |
| 5,693,088 A | 12/1997 | Lazarus | |
| 5,755,735 A | 5/1998 | Richter et al. | |
| 5,755,773 A | 5/1998 | Evans et al. | |
| 5,769,885 A | 6/1998 | Quiachon et al. | |
| 5,782,909 A | 7/1998 | Quiachon et al. | |
| 5,800,508 A | 9/1998 | Goicoechea et al. | |
| 5,800,512 A | 9/1998 | Lentz et al. | |
| 5,824,036 A | 10/1998 | Lauterjung | |
| 5,824,037 A | 10/1998 | Fogarty et al. | |
| 5,824,039 A | 10/1998 | Piplani et al. | |

(Continued)

FOREIGN PATENT DOCUMENTS

WO    WO 00/74598    12/2000

(Continued)

*Primary Examiner*—Alvin J. Stewart
(74) *Attorney, Agent, or Firm*—RatnerPrestia

(57) ABSTRACT

A stent-graft is provided that includes a bifurcated stent adapted for placement at the bifurcation of a bifurcated body lumen. The stent-graft further includes a graft that lines or covers at least part of the bifurcated stent. The graft defines a fluid passageway from the unbifurcated portion into one of the bifurcated stent branches. A closure prevents fluid from flowing through the second of the branches and into the other branch of the body lumen.

6 Claims, 3 Drawing Sheets

U.S. PATENT DOCUMENTS

| | | | |
|---|---|---|---|
| 5,843,160 A * | 12/1998 | Rhodes | 623/1.35 |
| 5,851,228 A | 12/1998 | Pinheiro | |
| 5,876,432 A | 3/1999 | Lau et al. | |
| 5,904,713 A | 5/1999 | Leschinsky | |
| 5,916,263 A | 6/1999 | Goicoechea et al. | |
| 5,984,955 A | 11/1999 | Wisselink | |
| 6,033,435 A | 3/2000 | Penn et al. | |
| 6,036,724 A | 3/2000 | Lentz et al. | |
| 6,051,020 A | 4/2000 | Goicoechea et al. | |
| 6,053,939 A | 4/2000 | Okuda et al. | |
| 6,080,191 A | 6/2000 | Summers | |
| 6,086,611 A | 7/2000 | Duffy et al. | |
| 6,099,560 A | 8/2000 | Penn et al. | |
| 6,102,938 A | 8/2000 | Evans et al. | |
| 6,129,756 A | 10/2000 | Kugler et al. | |
| 6,156,063 A | 12/2000 | Douglas | |
| 6,159,239 A | 12/2000 | Greenhalgh | |
| 6,162,246 A | 12/2000 | Barone | |
| 6,200,339 B1 | 3/2001 | Leschinsky et al. | |
| 6,251,133 B1 | 6/2001 | Richter et al. | |
| 6,261,316 B1 | 7/2001 | Shaolian et al. | |
| 6,270,525 B1 * | 8/2001 | Letendre et al. | 623/1.35 |
| 6,287,335 B1 | 9/2001 | Drasler et al. | |
| 6,290,731 B1 * | 9/2001 | Solovay et al. | 623/1.16 |
| 6,306,164 B1 * | 10/2001 | Kujawski | 623/1.35 |
| 6,312,462 B1 | 11/2001 | McDermott et al. | |
| 6,325,819 B1 * | 12/2001 | Pavcnik et al. | 623/1.11 |
| 6,334,869 B1 | 1/2002 | Leonhardt et al. | |
| 6,344,056 B1 | 2/2002 | Dehdashtian | |
| 6,398,807 B1 | 6/2002 | Chouinard et al. | |
| 6,409,750 B1 | 6/2002 | Hyodoh et al. | |
| 6,416,542 B1 | 7/2002 | Marcade et al. | |
| 6,428,565 B1 | 8/2002 | Wisselink | |
| 6,464,721 B1 | 10/2002 | Marcade et al. | |
| 6,475,238 B1 | 11/2002 | Fedida | |
| 6,576,009 B2 | 6/2003 | Ryan et al. | |
| 6,585,758 B1 | 7/2003 | Chouinard et al. | |
| 6,610,087 B1 | 8/2003 | Zarbatany et al. | |
| 6,652,571 B1 | 11/2003 | White et al. | |
| 6,676,699 B2 * | 1/2004 | Shiu | 623/1.24 |
| 6,685,738 B2 | 2/2004 | Chouinard et al. | |
| 6,752,826 B2 | 6/2004 | Holloway et al. | |
| 2002/0128703 A1 * | 9/2002 | Ravenscroft | 623/1.13 |
| 2003/0130725 A1 | 7/2003 | DePalma et al. | |
| 2004/0186560 A1 | 9/2004 | Alt | |
| 2004/0215327 A1 | 10/2004 | Doig et al. | |
| 2004/0215328 A1 | 10/2004 | Thornton | |

FOREIGN PATENT DOCUMENTS

| | | |
|---|---|---|
| WO | WO 02/24247 | 3/2002 |

* cited by examiner

ONE-BRANCH STENT-GRAFT FOR BIFURCATED LUMENS

This application is a divisional of application Ser. No. 10/461,898 filed on Jun. 13, 2003 now abandoned entitled ONE-BRANCH STENT-GRAFT FOR BIFURCATED LUMENS.

FIELD OF THE INVENTION

The present invention relates to a one-branch stent-graft for use in bifurcated body lumens. More specifically, the present invention relates to a stent graft including two branches, wherein a closure prevents fluid from flowing to one of the branches.

BACKGROUND OF THE INVENTION

A stent-graft (a stent with a graft layer lining or covering it) is typically used to provide a prosthetic intraluminal wall, e.g., in the case of a stenosis or aneurysm, to provide an unobstructed conduit for blood in the area of the stenosis or aneurysm. A stent-graft may be endoluminally deployed in a body lumen, a blood vessel for example, at the site of a stenosis or aneurysm by so-called "minimally invasive techniques" in which the stent-graft is compressed radially inwards and is delivered by a catheter to the site where it is required, through the patient's skin, or by a "cut down" technique at a location where the blood vessel concerned is accessible. When the stent-graft is positioned at the correct location, the stent-graft is caused or allowed to re-expand to a predetermined diameter in the vessel.

A one branch design stent-graft is typically utilized at a native vessel bifurcation to direct fluid into only one of the branches of the bifurcation. For example, an aorto-uni-iliac stent-graft provides an unobstructed conduit for blood to flow from the aorta through only one of the two iliacs. As used in the aorta, blood flows through the single branch stent-graft to the bifurcated vessel branch of the native bifurcation that contains the stent-graft, while blood is prevented from flowing to the other bifurcated branch of the native bifurcation.

Typical single branch design stent-grafts have a tendency to work their way distally from the originally deployed position. It will be appreciated by a person skilled in the art that it is desirable to prevent stents from migrating out of position. In particular, where the site of desired application of the stent or prosthesis is a native vessel bifurcation, the distal migration associated with the use of the prior art prostheses constitutes a significant disadvantage.

SUMMARY OF THE INVENTION

A stent-graft of this invention includes a bifurcated stent, i.e., an unbifurcated portion in fluid communication with two branches. The stent-graft further includes a graft that lines or covers at least part of the bifurcated stent. The graft of this stent graft defines a fluid passageway from the unbifurcated portion into one of the bifurcated stent branches. A closure, which may be part of the graft, prevents fluid from flowing to the other of the branches. The stent-graft is preferably adapted for placement of the stent bifurcation adjacent the native bifurcation of a body lumen to resist distal migration of the stent-graft. One use of such stent-grafts is in bypassing abdominal aortic aneurysms where a femoral-femoral bypass is surgically installed to provide blood flow to the occluded iliac.

According to one aspect of this invention, a stent-graft is provided that is adapted for placement at a native vessel bifurcation. The stent-graft includes a bifurcated stent with a proximal portion adapted for placement in an unbifurcated region of the native bifurcation. As used herein, the term "proximal" means the unbifurcated end of the stent or stent-graft, i.e., nearest to the heart when the bifurcated lumen is the abdominal aorta, and the term "distal" means the opposite, i.e., the bifurcated end of the stent or stent-graft. The bifurcated stent further includes two distal portions. The first distal portion is adapted to extend from the unbifurcated region of the native bifurcation into one of the bifurcated branches of the native bifurcation. The second distal portion extends toward and into the other bifurcated branch of the native bifurcation. A graft lining defines a fluid passage that extends from the proximal portion of the bifurcated stent to the first distal portion of the bifurcated stent. The graft lining is closed to the other of the bifurcated branches.

According to yet another aspect of this invention, a stent-graft adapted for placement at a native vessel bifurcation includes a bifurcated stent with a proximal portion adapted for placement in an unbifurcated region of the native bifurcation. The bifurcated stent further includes two distal portions. The first distal portion is adapted to extend from the unbifurcated region of the native bifurcation into one of the bifurcated branches of the native bifurcation. The second distal portion extends toward and into the other bifurcated branch of the native bifurcation. A graft lining or covering defines a fluid passage that extends from the proximal portion of the bifurcated stent to the distal portions of the bifurcated stent. An occluder device is adapted for placement in the second distal portion. The occluder prevents fluid passage through the second distal portion of the bifurcated stent-graft and to the second branch of the bifurcated lumen.

According to another aspect of this invention, a stent-graft is provided that is adapted for placement at a native vessel bifurcation. The stent-graft includes a straight bifurcated stent-graft and a tapered stent-graft. The straight bifurcated stent-graft includes a proximal portion adapted for placement in an unbifurcated region of the native bifurcation, and two distal portions. The first distal portion is adapted to extend from the unbifurcated region of the native bifurcation into one of the bifurcated branches of the native bifurcation. The second distal portion extends toward and into the other bifurcated branch of the native bifurcation. A graft lining or covering extends from the proximal portion of the straight bifurcated stent-graft to the distal portions of the straight bifurcated stent-graft. The tapered stent-graft includes a proximal tapered portion and a distal portion. The proximal portion is adapted for placement in the unbifurcated portion of the straight stent-graft and the distal portion is adapted for placement in the first distal portion of the straight stent-graft. A graft lining or covering extends from the proximal portion of the tapered stent-graft to the distal portion of the tapered stent-graft. The tapered stent-graft defines a fluid passage to the first distal-portion of the straight bifurcated stent-graft, and is closed to fluid passage into the second distal portion of the straight bifurcated stent-graft by the graft lining or covering of the tapered stent-graft.

BRIEF DESCRIPTION OF THE DRAWINGS

The aspects, features, and advantages of the present invention will be more readily understood from the following detailed description when read in conjunction with the accompanying drawings, in which.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the true spirit and scope of the present invention.

Figure 1A:
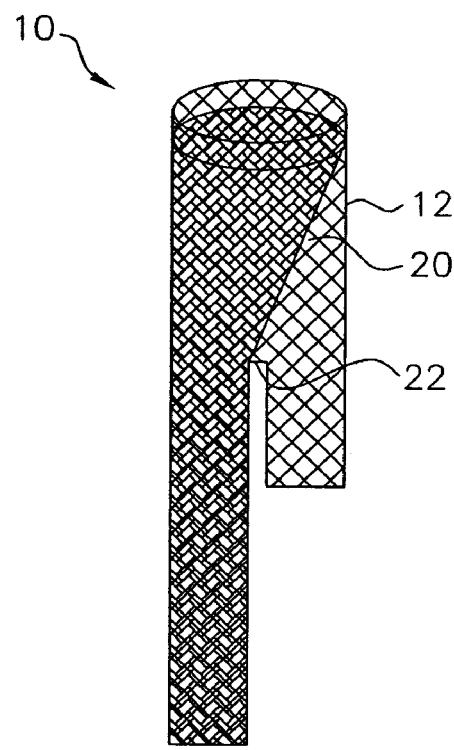
FIG. 1A is a front view of a stent-graft including a bifurcated stent and a graft lining in accordance with one embodiment of the present invention.
Figure 1B:
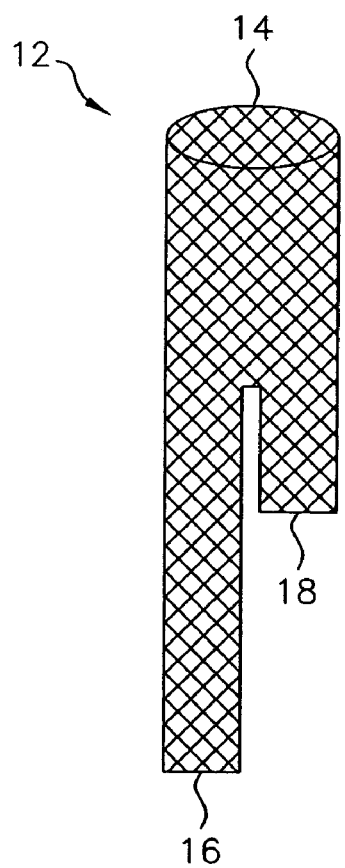
FIG. 1B is a detail view of the bifurcated stent of FIG. 1A.
Figure 1C:
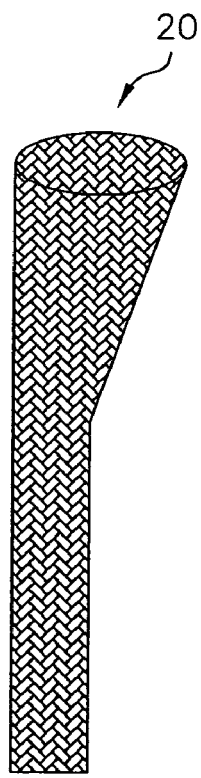
FIG. 1C is a detail view of the graft lining of FIG. 1A.

Referring specifically to FIGS. 1A-1C, there is shown a stent-graft 10 is adapted for placement at a native vessel bifurcation. The stent-graft 10 includes a bifurcated stent 12 with a proximal portion 14 adapted for placement in an unbifurcated region of the native bifurcation. The bifurcated stent 12 further includes two distal portions 16, 18. The first distal portion 16 is adapted to extend from the unbifurcated region of the native bifurcation into one of the bifurcated branches of the native bifurcation. The second distal portion 18 extends toward the other bifurcated branch of the native bifurcation. A graft lining 20 defines a fluid passage that extends from the proximal portion 14 of the bifurcated stent 12 to the distal portion 16 of the bifurcated stent 12. The graft lining 20 is adapted to extend to one of the bifurcated branches of the native bifurcation, but is closed to the other of the bifurcated branches. The stent-graft 10 is adapted for placement of the stent bifurcation 22 adjacent the native bifurcation.

FIG. 1B is a detail view of the bifurcated stent 12 illustrated in FIG. 1A. Typically, the bifurcated stent 12 has a radially compressed configuration for introduction into a lumen, and a radially expanded configuration for deployment within the lumen. In other words, the bifurcated stent 12 is compressed radially inwards and is delivered by a catheter to the site where it is required through the patient's skin, or by a "cut down" technique in which the blood vessel concerned is exposed by minor surgical means at an accessible location thereof. When the stent 12 is positioned at the correct location, the stent 12 is caused or allowed to re-expand to a predetermined diameter in the vessel and the catheter is withdrawn.

FIG. 1C is a detail view of the graft lining 20 illustrated in FIG. 1A. The graft lining 20 is attached to an inside surface of the bifurcated stent 12 (as illustrated in FIG. 1A) by sewing, suturing, or bonding.

In use, the stent-graft 10 illustrated in FIG. 1A is juxtaposed or extends across a bifurcation in an artery or vein such as, for example, the bifurcation in the mammalian aortic artery into the common iliac arteries. Such bifurcation is referred to throughout this specification as a native vessel bifurcation. In the case of an abdominal aortic aneurysm ("AAA") in the infrarenal portion of the aorta, which extends into one of the common iliac arteries, the stent-graft 10 is deployed such that the stent bifurcation 22 is placed adjacent the native vessel bifurcation. The first distal portion 16 extends into one of the bifurcated branches of the native bifurcation, while the second distal portion 18 extends toward and into the other bifurcated branch of the native bifurcation. The tapered shape of the graft lining 20 results in a fluid passage that extends from the proximal portion 14 of the bifurcated stent 12 to the first distal portion 16 of the bifurcated stent 12. In other words, blood flows through the stent-graft 10 to the bifurcated vessel branch of the native bifurcation that contains the first distal portion 16, while blood is prevented from flowing through the stent-graft 10 to the other bifurcated branch of the native bifurcation that contains the second distal portion 18.

Accordingly, the second distal portion 18 functions not as a fluid passageway, but as a structural member. The relationship among the first distal. portion 16, the stent bifurcation 22, and the second distal portion 18, allows the stent graft 10 to straddle or span the native vessel bifurcation when deployed, placing the stent bifurcation 22 adjacent the native vessel bifurcation tending to prevent distal migration. Actual contact between the stent bifurcation 22 and the native vessel bifurcation may prevent the stent-graft 10 from working its way down away from its originally deployed position.

In this and other embodiments of the present invention, the stent and graft, respectively, may be formed of conventional materials, such as nitinol and ePTFE.

Figure 2A:
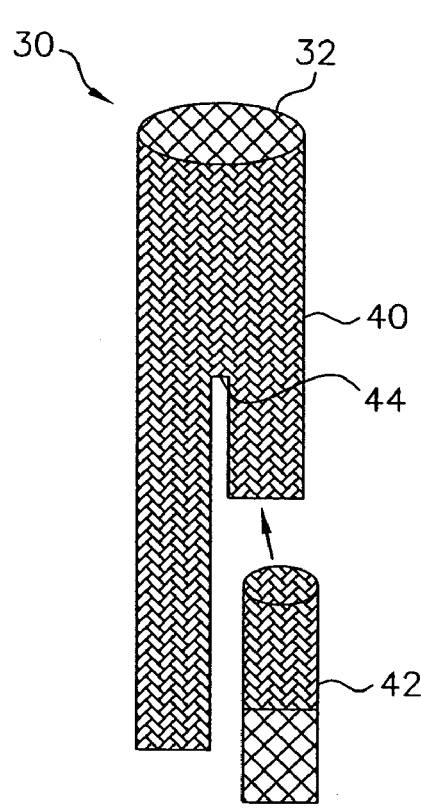
FIG. 2A is a front view of a stent-graft including a bifurcated stent, a graft lining, and an occluder device in accordance with another embodiment of the present invention.

Referring to FIGS. 2A-2D, there is shown another stent-graft 30, adapted for placement at a native vessel bifurcation, includes a bifurcated stent 32 with a proximal portion 34 adapted for placement in an unbifurcated region of the native bifurcation. The bifurcated stent 32 further includes two distal portions 36 and 38. The first distal portion 36 is adapted to extend from the unbifurcated region of the native bifurcation into one of the bifurcated branches of the native bifurcation. The second distal portion 38 extends toward and into the other bifurcated branch of the native bifurcation. A graft lining or covering 40 (graft covering 40 is represented in FIG. 2A) defines a fluid passage that extends from the proximal portion 34 of the bifurcated stent 32 to the distal portions 36 and 38 of the bifurcated stent 32. An occluder device 42 is adapted for placement in the second distal portion 38. The occluder 42 prevents fluid passage through the second distal portion 38 and to one of the bifurcated branches of the native bifurcation. The stent-graft 30 is adapted for placement of the stent bifurcation 44 adjacent the native bifurcation.

Figure 2B:
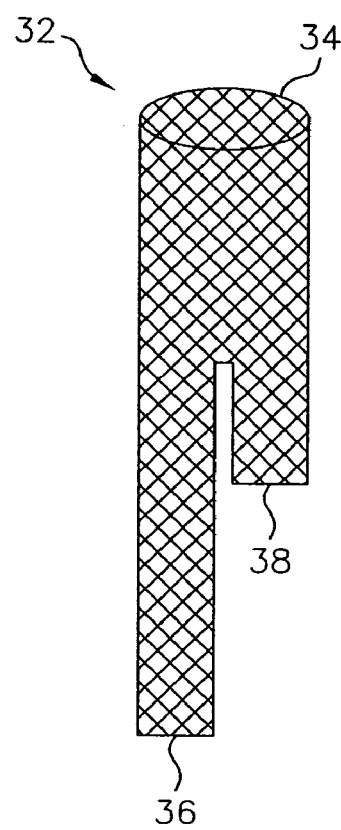
FIG. 2B is a detail view of the bifurcated stent of FIG. 2A.

FIG. 2B is a detail view of the bifurcated stent 32 illustrated in FIG. 2A. The bifurcated stent 32 has a radially compressed configuration for introduction into a lumen, and a radially expanded configuration for deployment within the lumen. In other words, the bifurcated stent 32 is compressed radially inwards and is delivered by a catheter to the site where it is required through the patient's skin, or by a "cut down" technique in which the blood vessel concerned is exposed by minor surgical means. When the stent 32 is positioned at the correct location, the stent 32 is caused or allowed to re-expand to a predetermined diameter in the vessel.

Figure 2C:
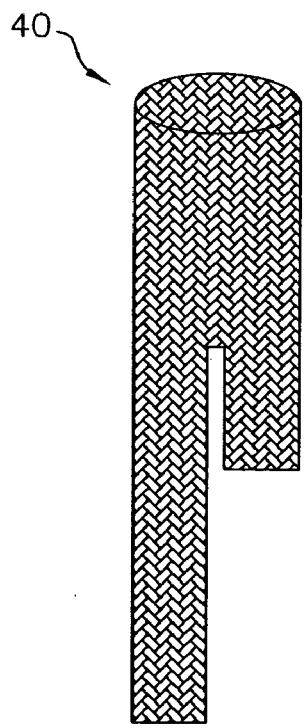
FIG. 2C is a detail view of the graft lining of FIG. 2A.

FIG. 2C is a detail view of the graft lining or covering 40 illustrated in FIG. 2A. The graft lining or covering 40 may be attached to an inside surface of the bifurcated stent 32, functioning as a lining. Alternatively, the graft lining or covering 40 may be attached to an outside surface of the bifurcated stent 32 (as illustrated in FIG. 2A), functioning as a covering.

Figure 2D:
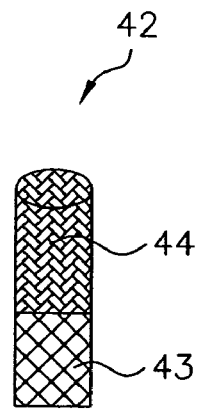
FIG. 2D is a detail view of the occluder device of FIG. 2A.

FIG. 2D is a detail view of one form of occluder useful in combination with stent graft 30. Specifically shown is an occluder device 42 comprising a closed, straight stent-graft, typically adapted for endoluminal delivery into the second distal portion 38 of the bifurcated stent 32 after the stent-graft 30 has been deployed and expanded. Similar to the bifurcated stent 32, occluder device 42 has a radially compressed configuration for introduction into a lumen, and a radially expanded configuration for deployment within the lumen. Occluder device 42 includes a stent 43 and a graft 44, either lining or covering part or all of stent 43 (as illustrated in FIGS. 2A and 2D). Graft 43, however, is closed at one end to occlude fluid flow through the occluder device 42 and thus through the second distal portion 38 of the stent-graft 30.

In use, stent-graft 30 is juxtaposed or extends across a bifurcation in an artery or vein. Bifurcated stent 32 is deployed such that stent bifurcation 44 is placed near or adjacent the native vessel bifurcation. First distal portion 36 extends into one of the bifurcated branches of the native bifurcation, while the second distal portion 38 extends toward and into the other bifurcated branch of the native bifurcation. After stent-graft 30 has been deployed and expanded, occluder device 42 is placed in the second distal portion 38 of the bifurcated stent 32, so that graft 43 defines a closed fluid passage, by which occluder device 42 prevents fluid from flowing through second distal portion 38 of bifurcated stent 32. Such a configuration results in a fluid passage that extends from proximal portion 34 of bifurcated stent 32 to first distal portion 36 of bifurcated stent 32. In other words, blood flows through the stent-graft 30 to the bifurcated vessel branch of the native bifurcation that contains the first distal portion 36, while blood is prevented from flowing through stent-graft 30 to the other bifurcated branch of the native bifurcation that contains second distal portion 38.

Accordingly, second distal portion 38 of stent 34 functions not as a fluid passageway, but as a structural member. The relationship among the first distal portion 36, the stent bifurcation 44, and the second distal portion 38, allows stent-graft 30 to straddle or span the native vessel bifurcation when deployed, placing the stent bifurcation 44 adjacent the native vessel bifurcation. Such a configuration tends to resist distal migration. Preferably, contact between the stent bifurcation 44 and the native vessel bifurcation prevents the stent-graft 30 from working its way down away from its originally deployed position.

Figure 3A:
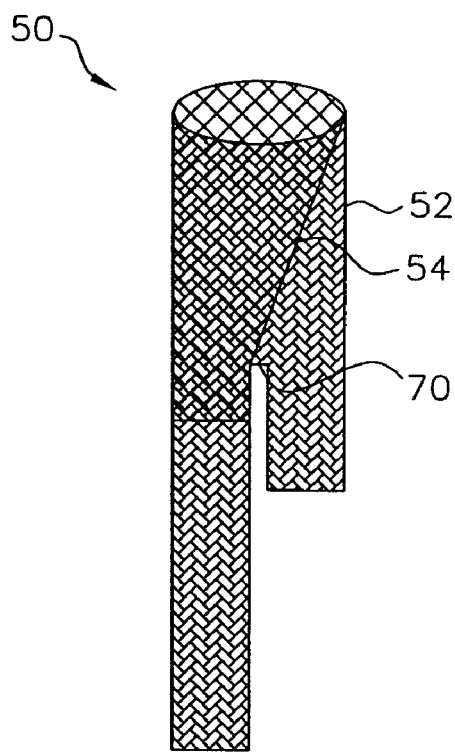
FIG. 3A is a front view of a stent-graft including a straight bifurcated stent and graft and a tapered stent and graft in accordance with yet another embodiment of the present invention.
Figure 3B:
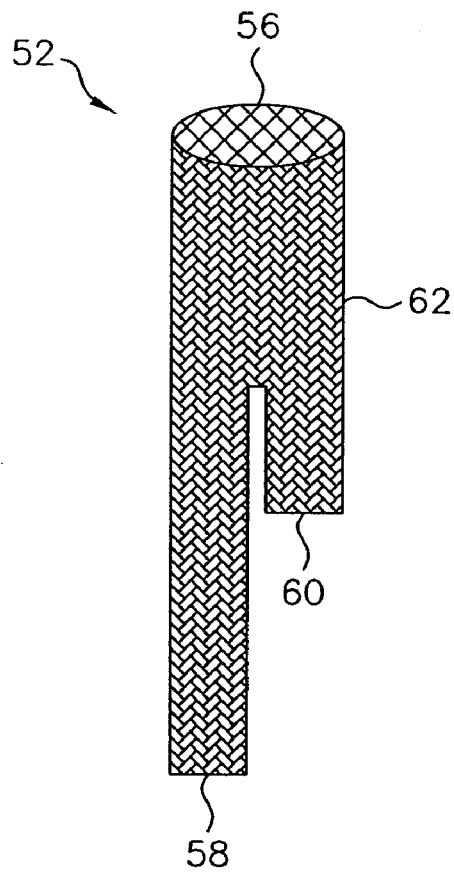
FIG. 3B is a detail view of the straight bifurcated stent and graft of FIG. 3A.
Figure 3C:
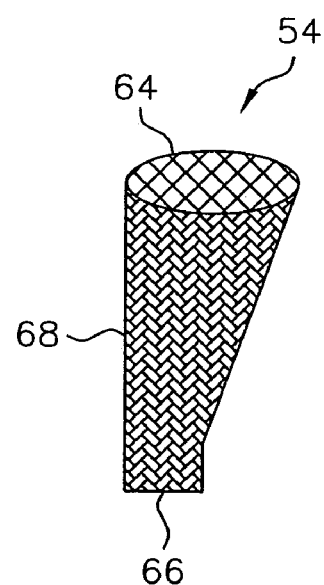
FIG. 3C is a detail view of the tapered stent and graft of FIG. 3A.

Referring to FIGS. 3A-3C, there is shown a stent-graft 50 adapted for placement at a native vessel bifurcation. Stent-graft 50 includes a straight bifurcated stent-graft 52 and a tapered stent-graft 54. Straight bifurcated stent-graft 52 includes a proximal portion 56 adapted for placement in an unbifurcated region of the native bifurcation, and two distal portions 58 and 60. First distal portion 58 is adapted to extend from the unbifurcated region of the native bifurcation into one of the bifurcated branches of the native bifurcation. Second bifurcation 60 extends toward and into the other bifurcated branch of the native bifurcation. A graft lining or covering 62 (graft covering 62 is represented in FIG. 3B) extends from proximal portion 56 of straight bifurcated stent-graft 52 to distal portions 58 and 60 of straight bifurcated stent-graft 52. Tapered stent-graft 54 includes a proximal tapered portion 64 and a distal portion 66. Distal portion 66 is adapted for placement, after the straight stent-graft 52 has been deployed and expanded, in proximal portion 56 and first distal portion 58 of straight bifurcated stent-graft 52. A graft lining or covering 68 (graft covering 68 is represented in FIG. 3A) extends from proximal portion 64 of the tapered stent-graft 54 to distal portion 66 of tapered stent-graft 54. Tapered stent-graft 54 defines a closed fluid passage to first distal portion 58 of straight bifurcated stent-graft 52, and is closed to fluid passage into second distal portion 60 of straight bifurcated stent-graft 52.

FIGS. 3B and 3C are detail views of the straight bifurcated stent-graft 52 and the tapered stent-graft 54, respectively, illustrated in FIG. 3A. Both stent-grafts 52 and 54 have a radially compressed configuration for introduction into a lumen, and a radially expanded configuration for deployment within the lumen. In other words, the stent-grafts 52 and 54 are compressed radially inwards and are delivered by a catheter to the site where it is required through the patient's skin, or by a "cut down" technique in which the blood vessel concerned is exposed by minor surgical means. When the stent-grafts 52 and 54 are positioned at the correct location, the stent-grafts 52 and 54 are caused or allowed to re-expand to a predetermined diameter in the vessel.

Graft linings or coverings 62 and 68 may be attached to an inside surface of each respective stent 52 and 54, functioning as linings. Alternatively, graft linings or coverings 62 and 68 may be attached to an outside surface of each respective stent 52 and 54 (as illustrated in FIGS. 3A-3B), functioning as a covering.

In use, the stent-graft 50 illustrated in FIG. 3A is juxtaposed or extends across a bifurcation in an artery or vein. The straight bifurcated stent-graft 52 is deployed such that the stent bifurcation 70 is placed near or adjacent the native vessel bifurcation. The first distal portion 58 extends into one of the bifurcated branches of the native bifurcation, while the second distal portion 60 extends into the other bifurcated branch of the native bifurcation. The tapered stent-graft 54 is positioned such that the distal portion 66 is placed in proximal portion 56 and in first distal portion 58 of straight bifurcated stent-graft 52. Graft lining or covering 68 of tapered stent-graft 54 defines a fluid passage that extends from proximal portion 56 of the straight bifurcated stent-graft 52 to first distal portion 58 of the straight bifurcated stent-graft 52. In other words, blood flows through the stent graft 50 exclusively to the bifurcated vessel branch of the native bifurcation that contains the first distal portion 58, while blood is prevented from flowing through the stent-graft 50 to the other bifurcated branch of the native bifurcation that contains second distal portion 60.

Accordingly, second distal portion 60 functions not as a fluid passageway, but as a structural member. The relationship among the first distal portion 58, the stent bifurcation 70, and the second distal portion 60, allows the stent-graft 50 to straddle or span the native vessel bifurcation when deployed, placing the stent bifurcation 70 adjacent the native vessel bifurcation to prevent distal migration of the device. Contact between the stent bifurcation 70 and the native vessel bifurcation may prevent stent-graft 50 from working its way down away from its originally deployed position.

While certain embodiments of the invention have been shown and described herein, it will be understood that such embodiments are provided by way of example only. Other embodiments may be devised by those skilled in the art utilizing the essential novelty of the invention as disclosed herein. It is intended that the appended claims be construed to include all such embodiments, whether or not disclosed herein.

The invention claimed is:

1. A stent-graft for bypassing one branch of a bifurcated body lumen, the body lumen having an unbifurcated region and at least two bifurcated branches extending therefrom, the stent-graft comprising:

a bifurcated stent, wherein said stent includes an unbifurcated portion and a first branch and a second branch extending therefrom, the unbifurcated portion being adapted for placement in the unbifurcated region of the body lumen and the first and second branches being adapted to each extend into one of the bifurcated branches of the body lumen;

a graft lining or covering which lines or covers at least part of said bifurcated stent and defines a fluid passageway from said unbifurcated portion into the first branch; and a second stent-graft having a fluid passage allowing fluid flow to the first branch and a closure preventing fluid flowing to the second branch, wherein said closure is placed in said unbifurcated portion of said bifurcated stent and extends into only the first branch of said bifurcated stent.

2. The stent-graft recited in claim 1, wherein said bifurcated stent has a radially compressed configuration for introduction into the bifurcated body lumen and a radially expanded configuration for deployment within the bifurcated body lumen.

3. The stent-graft recited in claim 1, wherein said second stent-graft has a radially compressed configuration for introduction into said bifurcated stent and a radially expanded configuration for deployment within said bifurcated stent.

4. A stent-graft, adapted for placement at a native vessel bifurcation, comprising:

a straight bifurcated stent including, a proximal portion adapted for placement in an unbifurcated region of the native bifurcation, two distal portions, the first of which is adapted to extend from the unbifurcated region of the native bifurcation into one of the bifurcated branches of the native bifurcation, the second of which is adapted to extend toward the other bifurcated branch of the native bifurcation, and a graft lining or covering which extends from said proximal portion of said straight bifurcated stent to said distal portions of said straight bifurcated stent; and a tapered stent including, a proximal tapered portion adapted for placement in said proximal portion of said straight bifurcated stent, a distal portion adapted for placement in said first distal portion of said straight bifurcated stent, and a graft lining or covering which extends from said proximal portion of said tapered stent to said distal portion of said tapered stent, wherein said tapered stent defines a fluid passage to said first distal portion of said straight bifurcated stent, and is closed to fluid passage into said second distal portion of said straight bifurcated stent.

5. The stent-graft recited in claim 4, wherein said straight bifurcated stent has a radially compressed configuration for introduction into a lumen and a radially expanded configuration for deployment within the lumen.

6. The stent graft recited in claim 4, wherein said tapered stent has a radially compressed configuration for introduction into a lumen and a radially expanded configuration for deployment within the lumen.

* * * * *

UNITED STATES PATENT AND TRADEMARK OFFICE
CERTIFICATE OF CORRECTION

PATENT NO. : 7,491,231 B2
APPLICATION NO. : 10/963354
DATED : February 17, 2009
INVENTOR(S) : Nazzaro et al.

It is certified that error appears in the above-identified patent and that said Letters Patent is hereby corrected as shown below:

Column 7, lines 12 and 13, "a closure preventing fluid flowing" should read --a closure preventing fluid from flowing--.

Signed and Sealed this

Twelfth Day of May, 2009

JOHN DOLL
*Acting Director of the United States Patent and Trademark Office*